(12) United States Patent
Berge et al.

(10) Patent No.: US 7,351,696 B2
(45) Date of Patent: Apr. 1, 2008

(54) COMPOUNDS

(75) Inventors: John Michael Berge, Harlow (GB); Catherine Simone Victoire Frydrych, Harlow (GB); Richard Lewis Jarvest, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 36 days.

(21) Appl. No.: 10/533,461

(22) PCT Filed: Oct. 29, 2003

(86) PCT No.: PCT/EP03/12068

§ 371 (c)(1), (2), (4) Date: Nov. 17, 2005

(87) PCT Pub. No.: WO2004/039822

PCT Pub. Date: May 13, 2004

(65) Prior Publication Data

US 2007/0037757 A1    Feb. 15, 2007

(30) Foreign Application Priority Data

Oct. 31, 2002  (GB) ................................. 0225384.7

(51) Int. Cl.
*A61K 31/70* (2006.01)
*C07H 17/08* (2006.01)
(52) U.S. Cl. .......................................... 514/29; 536/7.4
(58) Field of Classification Search ................ 536/7.4; 514/29
See application file for complete search history.

(56) References Cited

U.S. PATENT DOCUMENTS

2002/0019355 A1   2/2002  Ma et al. ...................... 514/29

2005/0080025 A1*  4/2005  Alihodzic et al. ............ 514/29

FOREIGN PATENT DOCUMENTS

| EP | 0 284 203 | 9/1988 |
| EP | 0 895 999 A | 2/1999 |
| WO | WO 00/71557 | 11/2000 |
| WO | WO 01/63539 | 8/2001 |
| WO | WO 03/042228 | 5/2003 |

* cited by examiner

*Primary Examiner*—Elli Peselev
(74) *Attorney, Agent, or Firm*—Laura K. Madden; Loretta Sauermelch; Mary E. McCarthy

(57) ABSTRACT

The present invention relates to compounds of formula (I)

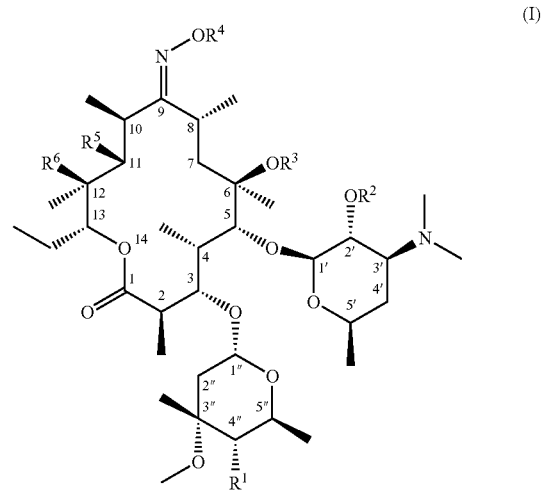

and pharmaceutically acceptable derivatives thereof, to processes for their preparation and their use in therapy or prophylaxis of systemic or topical microbial infections in a human or animal body.

12 Claims, No Drawings

COMPOUNDS

This application is a 371 of International Application No. PCT/EP2003/012068, filed 29 Oct. 2003.

The present invention relates to novel semi-synthetic macrolides having antimicrobial activity, in particular antibacterial activity. More particularly, this invention relates to novel oxime macrolide scaffolds substituted at the 4" position, to processes for their preparation, to compositions containing them and to their use in medicine.

Macrolide antibacterial agents are known to be useful in the treatment or prevention of bacterial infections. However, the emergence of macrolide-resistant bacterial strains has resulted in the need to develop new macrolide compounds. For example, EP 0 895 999 describes derivatives modified at the 4" position of the macrolide ring having antibacterial activity.

According to the present invention, we have now found novel oxime macrolide scaffolds substituted at the 4" position which also have antimicrobial activity.

Thus, the present invention provides compounds of general formula (I)

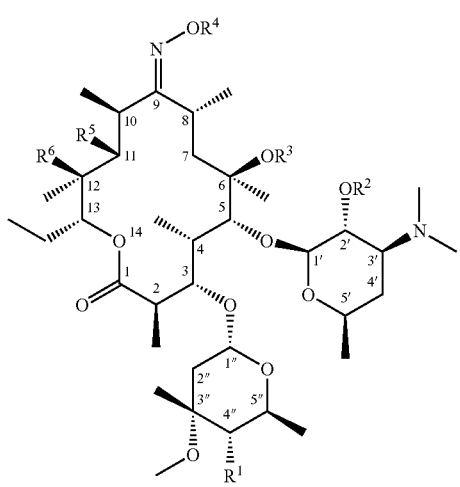

wherein
$R^1$ is $OC(O)(CH_2)_m XR^7$;
$R^2$ is hydrogen or a hydroxyl protecting group;
$R^3$ is hydrogen, $C_{1-4}$alkyl or $C_{3-6}$alkenyl optionally substituted by 9 to 10 membered fused bicyclic heteroaryl;
$R^4$ is hydrogen, $C_{1-4}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, $OR^8$, $S(O)_n R^8$, $NR^8 R^9$, $CONR^8 R^9$, halogen and cyano;
$R^5$ is hydroxy, $C_{3-6}$alkenyloxy optionally substituted by 9 to 10 membered fused bicyclic heteroaryl, or $O(CH_2)_p O(CH_2)_q R^{10}$,
$R^6$ is hydroxy, or
$R^5$ and $R^6$ taken together with the intervening atoms form a cyclic group having the following structure:

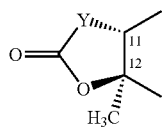

wherein Y is a bivalent radical selected from —$CH_2$—, —$CH(CN)$—, —O—, —$N(R^{11})$— and —$CH(SR^{11})$—;
$R^7$ is a heterocyclic group having the following structure:

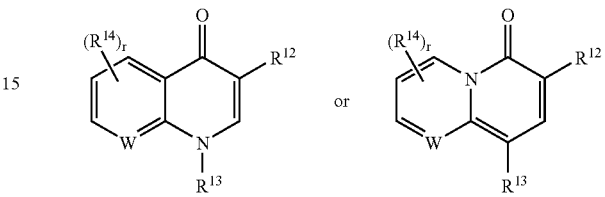

$R^8$ and $R^9$ are each independently selected from hydrogen and $C_{1-4}$alkyl;
$R^{10}$ is hydrogen or $NR^8 R^9$;
$R^{11}$ is hydrogen or $C_{1-4}$alkyl substituted by a group selected from optionally substituted phenyl, optionally substituted 5 or 6 membered heteroaryl and optionally substituted 9 to 10 membered fused bicyclic heteroaryl;
$R^{12}$ is hydrogen, $C(O)OR^{15}$, $C(O)NHR^{15}$ or $C(O)CH_2 NO_2$;
$R^{13}$ is hydrogen, $C_{1-4}$alkyl optionally substituted by hydroxy or $C_{1-4}$alkoxy, $C_{3-7}$cycloalkyl, or optionally substituted phenyl or benzyl;
$R^{14}$ is halogen, $C_{1-4}$alkyl, $C_{1-4}$thioalkyl, $C_{1-4}$alkoxy, $NH_2$, $NH(C_{1-4}alkyl)$ or $N(C_{1-4}alkyl)_2$;
$R^{15}$ is hydrogen or $C_{1-4}$alkyl optionally substituted by up to three groups independently selected from halogen, $C_{1-4}$alkoxy, $OC(O)C_{1-4}$alkyl and $OC(O)OC_{1-4}$alkyl;
$R^{16}$ is hydrogen, $C_{1-4}$alkyl, $C_{3-7}$cycloalkyl, optionally substituted phenyl or benzyl, acetyl or benzoyl;
$R^{17}$ is hydrogen or $R^{14}$, or $R^{17}$ and $R^{13}$ are linked to form the bivalent radical —$O(CH_2)_2$— or —$(CH_2)_v$—;
X is —$U(CH_2)_s Z$— or X is a group selected from:

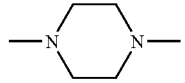

and

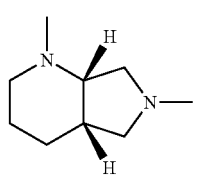

U and Z independently are a divalent radical selected from —$N(R^{16})$—, —O—, —$S(O)_t$—, —$N(R^{16})C(O)$—, —$C(O)N(R^{16})$— and —$N[C(O)R^{16}]$—;
W is $CR^{17}$ or a nitrogen atom;
m is 0 or an integer from 1 to 5;
n, r and t are each independently selected from 0, 1 and 2;
p and q are each independently selected from 1 to 6;
s is an integer from 2 to 8; and
v is 2 or 3;

and pharmaceutically acceptable derivatives thereof.

In one embodiment, the present invention provides compounds of general formula (IA)

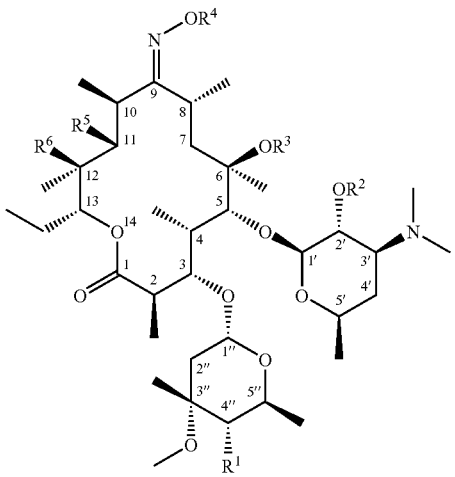
(IA)

wherein
$R^1$ is $OC(O)(CH_2)_m XR^7$;
$R^2$ is hydrogen or a hydroxyl protecting group;
$R^3$ is hydrogen, $C_{1-4}$alkyl or $C_{3-6}$alkenyl optionally substituted by 9 to 10 membered fused bicyclic heteroaryl;
$R^4$ is hydrogen, $C_{1-4}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, $OR^8$, $S(O)_n R^8$, $NR^8R^9$, $CONR^8R^9$, halogen and cyano;
$R^5$ is hydroxy, $C_{3-6}$alkenyloxy optionally substituted by 9 to 10 membered fused bicyclic heteroaryl or $O(CH_2)_p O(CH_2)_q R^{10}$,
$R^6$ is hydroxy, or
$R^5$ and $R^6$ taken together with the intervening atoms form a cyclic group having the following structure:

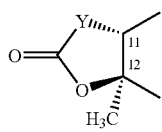

wherein Y is a bivalent radical selected from —$CH_2$—, —$CH(CN)$—, —$O$—, —$N(R^{11})$— and —$CH(SR_8)$—;
$R^7$ is a heterocyclic group having the following structure:

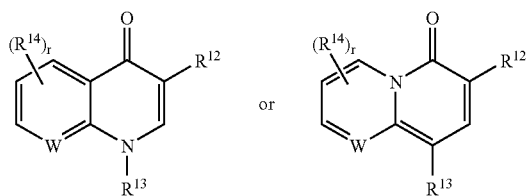

$R^8$ and $R^9$ are each independently selected from hydrogen and $C_{1-4}$alkyl;
$R^{10}$ is hydrogen or $NR^8R^9$;

$R^{11}$ is hydrogen or $C_{1-4}$alkyl substituted by a group selected from optionally substituted phenyl, optionally substituted 5 or 6 membered heteroaryl and optionally substituted 9 to 10 membered fused bicyclic heteroaryl;
$R^{12}$ is hydrogen, $C(O)OR^{15}$, $C(O)NHR^{15}$ or $C(O)CH_2NO_2$;
$R^{13}$ is hydrogen, $C_{1-4}$alkyl, $C_{3-7}$cycloalkyl, or optionally substituted phenyl or benzyl;
$R^{14}$ is halogen, $C_{1-4}$alkyl, $C_{1-4}$thioalkyl, $C_{1-4}$alkoxy, $NH_2$, $NH(C_{1-4}$alkyl) or $N(C_{1-4}$alkyl$)_2$;
$R^{15}$ is hydrogen or $C_{1-4}$alkyl;
$R^{16}$ is hydrogen, $C_{1-4}$alkyl, $C_{3-7}$cycloalkyl, optionally substituted phenyl or benzyl, acetyl or benzoyl;
X is —$U(CH_2)_s Z$— or X is a group selected from:

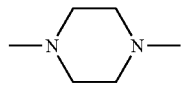

and

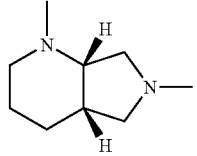

U and Z independently are a divalent radical selected from —$N(R^{16})$—, —$O$—, —$S(O)_t$—, —$N(R^{16})C(O)$—, —$C(O)N(R^{16})$— and —$N[C(O)R^{16}]$—;
W is a carbon or a nitrogen atom;
m is 0 or an integer from 1 to 5;
n, r and t are each independently selected from 0, 1 and 2;
p and q are each independently selected from 1 and 2; and
s is an integer from 2 to 8;

and pharmaceutically acceptable salts and solvates thereof.

The term "pharmaceutically acceptable" as used herein means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. In one embodiment, the pharmaceutically acceptable derivatives are salts and solvates. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The solvates may, for example, be hydrates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series, Edward B. Roche, ed., "Bioreversible Carriers in Drug Design", American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the invention include both compounds of formula (I) and their pharmaceutically acceptable derivatives. In particular, references hereinafter to a compound according to the invention include both compounds of formula (I) and their pharmaceutically acceptable acid addition salts together with pharmaceutically acceptable solvates.

The compound of formula (I) and salts thereof may form solvates (e.g. hydrates) and the invention includes all such solvates.

In the general formula (I) as drawn the solid wedge shaped bond indicates that the bond is above the plane of the paper. The broken bond indicates that the bond is below the plane of the paper.

Compounds wherein $R^2$ represents a hydroxyl protecting group are in general intermediates for the preparation of other compounds of formula (I).

When the group $OR^2$ is a protected hydroxyl group this is conveniently an ether or an acyloxy group. Examples of particularly suitable ether groups include those in which $R^2$ is a trialkylsilyl (i.e. trimethylsilyl). When the group $OR^2$ represents an acyloxy group, then examples of suitable groups $R^2$ include acetyl or benzoyl.

When $R^7$ is a heterocyclic group having the following structure:

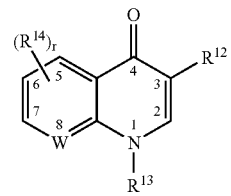

wherein W is $CR^{17}$ or nitrogen, where $R^{17}$ is hydrogen or $R^{14}$, said heterocyclic is linked in the 7 or 6 position to the Z group as above defined or to one of the nitrogen atoms contained in the following structures:

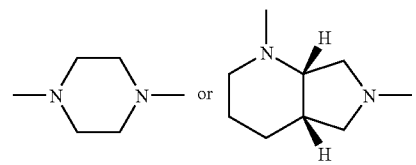

When $R^7$ is a heterocyclic group having the following structure:

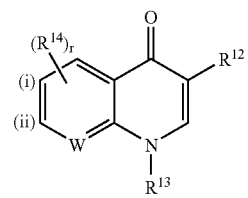

wherein W is $CR^{17}$, where $R^{17}$ and $R^{13}$ are linked to form the bivalent radical —O(CH$_2$)$_2$— or —(CH$_2$)$_v$—, said heterocyclic is linked in the (i) or (ii) position to the Z group as above defined or to one of the nitrogen atoms contained in the following structures:

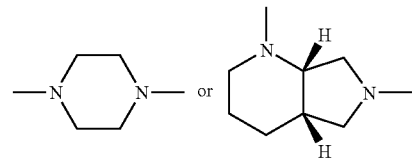

When $R^7$ is a heterocyclic group having the following structure:

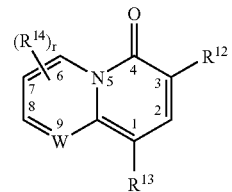

wherein W is $CR^{17}$, where $R^{17}$ is hydrogen or $R^{14}$, said heterocyclic is linked in the 8 or 7 position to the Z group as above defined or to one of the nitrogen atoms contained in the following structures:

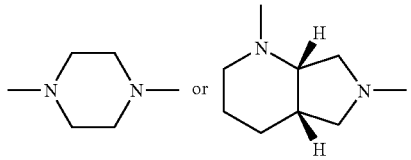

When $R^7$ is a heterocyclic group having the following structure:

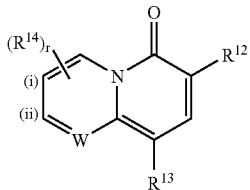

wherein W is $CR^{17}$, where $R^{17}$ and $R^{13}$ are linked to form the bivalent radical —O(CH$_2$)$_2$— or —(CH$_2$)$_v$—, said heterocyclic is linked in the (i) or (ii) position to the Z group as above defined or to one of the nitrogen atoms contained in the following structures:

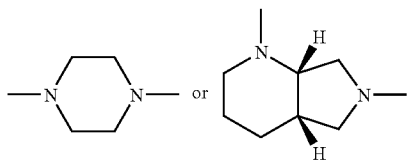

When $R^7$ is a heterocyclic group having the following structure:

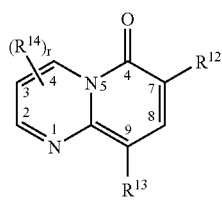

said heterocyclic is linked in the 2 or 3 position to the Z group as above defined or to one of the nitrogen atoms contained in the following structures:

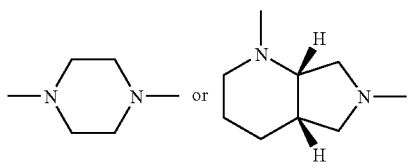

The term $C_{1-4}$alkyl as used herein as a group or a part of the group refers to a straight or branched alkyl group containing from 1 to 4 carbon atoms; examples of such groups include methyl, ethyl, propyl, isopropyl, n-butyl, isobutyl, tert-butyl.

The term $C_{2-6}$alkenyl group as used herein as a group or a part of the group refers to a straight or branched alkenyl group containing from 2 to 6 carbon atoms; examples of such groups include 2-propenyl, 1-propenyl, isopropenyl, 2-butenyl, 2-pentenyl, 2-hexenyl and the like. It will be appreciated that in groups of the form —O—$C_{2-6}$alkenyl, the double bond is preferably not adjacent to the oxygen.

The term $C_{3-7}$cycloalkyl group means a non-aromatic monocyclic hydrocarbon ring of 3 to 7 carbon atoms such as, for example, cyclopropyl, cyclobutyl, cyclopentyl, cyclohexyl or cycloheptyl.

The term 5 or 6 membered heteroaryl as used herein as a group or a part of the group refers to furanyl, thiophenyl, imidazolyl, oxazolyl, thiazolyl, pyrazolyl, pyridyl, pyridazinyl or pyrimidinyl.

The term 5 or 6 membered heterocyclic group as used herein as a group or part of the group refers to a monocyclic 5 or 6 membered saturated hydrocarbon ring containing at least one heteroatom independently selected from oxygen, nitrogen and sulfur. Examples of heterocyclyl groups include, but are not limited to, pyrrolidinyl, imidazolidinyl, pyrazolidinyl, piperidyl, piperazinyl, morpholino, tetrahydropyranyl, tetrahydrofuranyl, and thiomorpholino.

The term halogen refers to a fluorine, chlorine, bromine or iodine atom.

The term $C_{1-4}$alkoxy group may be a straight chain or a branched chain alkoxy group, for example methoxy, ethoxy, propoxy, prop-2-oxy, butoxy, but-2-oxy or 2-methylprop-2-oxy.

The term 9 to 10 membered fused bicyclic heteroaryl as used herein as a group or a part of the group refers to quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl or benzothiophenyl.

The terms optionally substituted phenyl, optionally substituted 5 or 6 membered heteroaryl, optionally substituted 9 to 10 membered fused bicyclic heteroaryl or optionally substituted 5 or 6 membered heterocyclic group refer to a group which is substituted by 1 to 3 groups selected from halogen, $C_{1-4}$alkyl, $C_{1-4}$alkoxy, hydroxy, nitro, cyano, amino, $C_{1-4}$alkylamino or di$C_{1-4}$ alkylamino, phenyl and 5 or 6 membered heteroaryl.

Preferred compounds of formula (I) are those wherein $R^2$ is hydrogen.

A representative example of $R^3$ is hydrogen.

In one embodiment, $R^4$ is hydrogen or $C_{1-4}$ alkyl optionally substituted by up to three substituents independently selected from optionally substituted 5 or 6 membered heteroaryl, $OR^8$, $S(O)_nR^8$, $NR^8R^9$, halogen and cyano. In another embodiment, $R^4$ is hydrogen or $C_{1-4}$alkyl optionally substituted by up to two substituents independently selected from optionally substituted 5 or 6 membered heteroaryl, $OR^8$, $S(O)_nR^8$, $NR^8R^9$, halogen and cyano. In another embodiment, $R^4$ is $C_{1-4}$alkyl optionally substituted by up to three substituents independently selected from optionally substituted 5 or 6 membered heteroaryl, $OR^8$, $S(O)_nR^8$, $NR^8R^9$, halogen and cyano. In a further embodiment, $R^4$ is $C_{1-4}$alkyl optionally substituted by up to two substituents independently selected from optionally substituted 5 or 6 membered heteroaryl, $OR^8$, $S(O)_nR^8$, $NR^8R^9$, halogen and cyano. Representative examples of $R^4$ include include hydrogen and $C_{1-4}$alkyl, for example methyl, ethyl, propyl or isopropyl, optionally substituted by optionally substituted 5 or 6 membered heteroaryl such as pyridyl, $OR^8$ or $S(O)_n R^8$. Additional representative examples of $R^4$ include $C_{1-4}$alkyl, for example methyl or isopropyl, optionally substituted by optionally substituted 5 or 6 membered heteroaryl such as pyridyl, $OR^8$ or $S(O)_n R^8$. Further representative examples of $R^4$ include include hydrogen and $C_{1-4}$alkyl, for example ethyl, propyl or isopropyl.

In one embodiment, $R^5$ is $O(CH_2)_p O(CH_2)_q R^{10}$, wherein $R^{10}$ is preferably $NR^8 R^9$. In another embodiment, $R^5$ is hydroxy. In a further embodiment, $R^6$ is hydroxy. Alternatively, $R^5$ and $R^6$ taken together with the intervening atoms form a cyclic group having the following structure:

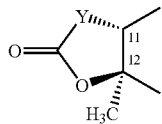

wherein Y is the bivalent radical —O—.

Representative examples of $R^7$ include heterocyclic groups having the following structure:

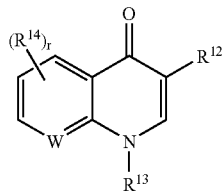

wherein W is preferably $CR^{17}$ where $R^{17}$ is hydrogen.

Representative examples of $R^8$ and $R^9$ include $C_{1-4}$ alkyl, for example methyl and ethyl.

A representative example of $R^{12}$ is $C(O)OR^{15}$, wherein $R^{15}$ is preferably hydrogen.

In one embodiment, $R^{13}$ is hydrogen, $C_{1-4}$alkyl, $C_{3-7}$cycloalkyl, or optionally substituted phenyl or benzyl. A representative example of $R^{13}$ is $C_{3-7}$cycloalkyl, for example $C_{3-6}$cycloalkyl such as cyclopropyl, cyclobutyl, cyclopentyl and cyclohexyl, in particular cyclopropyl.

Representative examples of $R^{14}$ include halogen, in particular fluorine and chlorine. When $R^7$ is a heterocyclic group having the following structure:

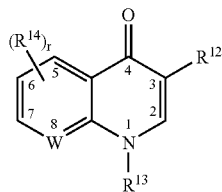

wherein W is preferably $CR^{17}$ where $R^{17}$ is hydrogen, $R^{14}$ is preferably fluorine or chlorine at the 6 or 7 position and the heterocyclic is linked in the unsubstituted 6 or 7 position to the X group.

In one embodiment, $R^{15}$ is hydrogen or $C_{1-4}$alkyl. Preferably, $R^{15}$ is hydrogen.

A representative example of X is —U(CH$_2$)$_s$Z-. In particular, X is —U(CH$_2$)$_s$Z- wherein U and Z are preferably —NH—. In another embodiment, X is —U(CH$_2$)$_s$Z- wherein U and Z are preferably independently —NH— or —O—.

In one embodiment, W is carbon i.e. $CR^{17}$ where $R^{17}$ is hydrogen or $R^{14}$, in particular where $R^{17}$ is hydrogen, or nitrogen Preferably m is 1 to 3, in particular 2.

A representative example of n is 0.

In one embodiment, p and q are each independently selected from 1 and 2. When p is 1, q is preferably 2.

A representative example of r is 1.

Preferably s is 2 to 4, in particular 2.

Particularly preferred compounds of the invention are:
4"-O-[3-[[2-[(3-carboxy-7-chloro-1-cyclopropyl-1,4-dihydro-4-oxo-6-quinolinyl) amino]ethyl]amino]propionyl]-11-O-(2-dimethylaminoethoxymethyl)-(9E) methoximino erythromycin A,
4"-O-[3-[[2-[(3-carboxy-7-chloro-1-cyclopropyl-1,4-dihydro-4-oxo-6-quinolinyl) amino]ethyl]amino]propionyl]-11,12-carbonate-(9E)-O-(2-propyl)oximino erythromycin A,
4"-O-[3-[[2-[(3-carboxy-7-chloro-1-cyclopropyl-1,4-dihydro-4-oxo-6-quinolinyl) amino]ethyl]amino]propionyl]-11,12-carbonate-(9E)-methoximino erythromycin A, and
4"-O-[3-[[2-[(3-carboxy-7-chloro-1-cyclopropyl-1,4-dihydro-4-oxo-6-quinolinyl) amino]ethyl]amino]propionyl]-11,12-carbonate-(9E)-O-(ethoxymethyl)oximino erythromycin A.

Compounds according to the invention also exhibit a broad spectrum of antimicrobial activity, in particular antibacterial activity, against a wide range of clinical pathogenic microorganisms. Using a standard microtiter broth serial dilution test, compounds of the invention have been found to exhibit useful levels of activity against a wide range of pathogenic microorganisims. In particular, the compounds of the invention may be active against strains of *Staphylococcus aureus, Streptopococcus pneumoniae, Moraxella catarrhalis, Streptococcus pyogenes, Haemophilus influenzae, Chiamydia pneumoniae, Mycoplasma pneumoniae* and *Legionella pneumophila*. The compounds of the invention may also be active against resistant strains, for example erythromycin resistant strains. In particular, the compounds of the invention may be active against erythromycin resistant strains of *Streptococcus pneumoniae* and *Streptococcus pyogenes*.

The compounds of the invention may therefore be used for treating a variety of diseases caused by pathogenic microorganisms, in particular bacteria, in human beings and animals.

Thus, according to another aspect of the present invention, we provide a compound of formula (I) or a physiologically acceptable derivative, for example salt, thereof for use in the therapy or prophylaxis of systemic or topical microbial infections, in particular bacterial infections, in a human or animal subject.

According to a further aspect of the invention we provide the use of a compound of formula (I) or a physiologically acceptable derivative, for example salt, thereof for the manufacture of a therapeutic agent for the treatment or prophylaxis of systemic or topical microbial infections, in particular bacterial infections, in a human or animal body.

According to a yet further aspect of the invention we provide a method of treatment of the human or non-human animal body to combat microbial infections, in particular bacterial infections, which method comprises administering to the body an effective amount of a compound of formula (I) or a physiologically acceptable derivative, for example salt, thereof.

While it is possible that, for use in therapy, a compound of the invention may be administered as the raw chemical it is preferable to present the active ingredient as a pharmaceutical formulation.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluorormethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01-99% of the active material. For topical administration, for example, the composition will generally contain from 0.01-10%, more preferably 0.01-1% of the active material.

For systemic administration the daily dose as employed for adult human treatment it will range from 2-100 mg/kg body weight, preferably 5-60 mg/kg body weight, which may be administered in 1 to 4 daily doses, for example, depending on the route of administration and the condition of the patient. When the composition comprises dosage units, each unit will preferably contain 200 mg to 1 g of active ingredient. The duration of treatment will be dictated by the rate of response rather than by arbitrary numbers of days.

Compounds of general formula (I) and derivatives thereof may be prepared by the general method outlined hereinafter. In the following description, the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, X, Y, U, Z, W, m, n, p, q, r, s, t and v have the meaning defined for the compounds of formula (I) unless otherwise stated. The groups $X^aR^{7a}$ and $Z^aR^{7a}$ are $XR^7$ and $ZR^7$ as defined for formula (I) or groups convertible to $XR^7$ and $ZR^7$ respectively. Conversion of a group $X^aR^{7a}$ or $Z^aR^{7a}$ to a $XR^7$ or $ZR^7$ group typically arises if a protecting group is needed during the reactions described below. A comprehensive discussion of the ways in which such groups may be protected and methods for cleaving the resulting protected derivatives is given in for example T. W. Greene and P. G. M Wuts in Protective Groups in Organic Synthesis $2^{nd}$ ed., John Wiley & Son, Inc 1991.

The compounds of general formula (I) and derivatives thereof may be purified by conventional methods known in the art. For example, the compounds may be purified by HPLC using an aqueous solution of an acid such as formic acid or trifluoroacetic acid.

Compounds of formula (I) wherein m is an integer 1 to 5, may be prepared by reaction of 4" hydroxy of formula (II) with a suitable activated and protected derivative of the carboxylic acid (III), followed where necessary by subsequent removal of the hydroxyl protecting group $R^2$ and conversion of the $X^aR^{7a}$ group to $XR^7$.

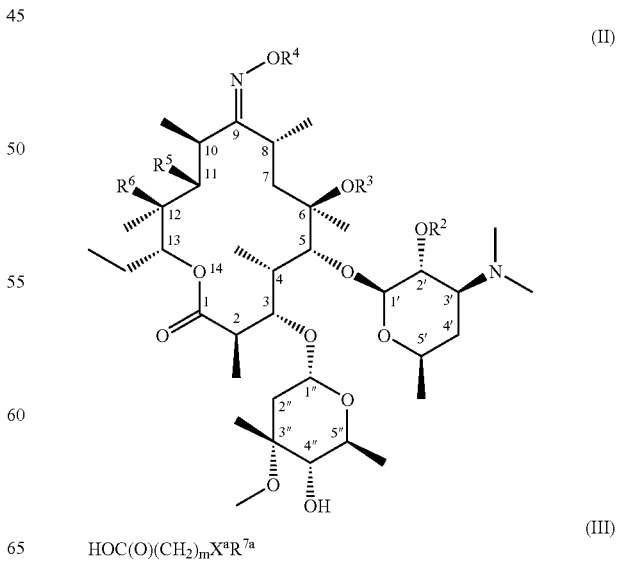

$$HOC(O)(CH_2)_m X^a R^{7a}$$ (III)

Suitable activated derivatives of the carboxyl group include the corresponding acyl halide, mixed anhydride or activated ester such as a thioester. The reaction is preferably carried out in a suitable aprotic solvent such as a halohydrocarbon (e.g. dichloromethane) or N,N-dimethylformamide optionally in the presence of a tertiary organic base such as dimethylaminopyridine or triethylamine or in the presence of inorganic base (i.e sodium hydride) and at a temperature within the range of 0° to 120° C.

Compounds of formula (I) wherein m is 0 and U is selected from —N($R^{16}$)—, —O— and —S(O)$_t$— wherein t is 0, may be prepared by reaction of compounds of formula (II), in which the 4" hydroxy is suitably activated, with a compound of formula $X^a R^{7a}$ (IV), followed where necessary by subsequent removal of the hydroxyl protecting group $R^2$ and conversion of the $X^a R^{7a}$ group to $XR^7$. Suitable activated derivatives of the 4" hydroxy group include for example carbonyl imidazole. The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine and at a temperature within the range of 0° to 120° C.

Compounds of formula (I) wherein m is 0 and U is —N($R^{16}$)C(O)—, may be prepared by reaction of compounds of formula (V),

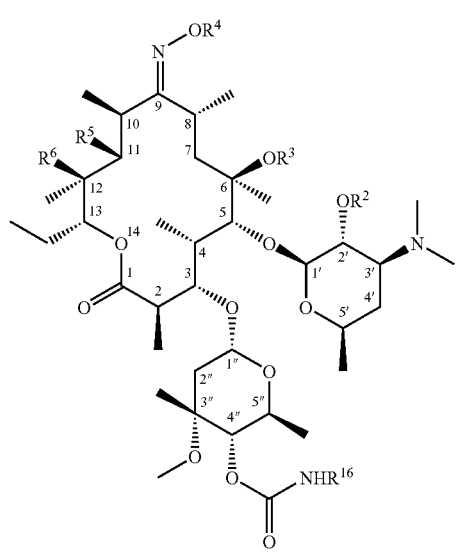

(V)

with a compound of formula HOC(O)(CH$_2$)$_s$$Z^a R^{7a}$ (VI), followed where necessary by subsequent removal of the hydroxyl protecting group $R^2$ and conversion of the $Z^a R^{7a}$ group to $ZR^7$. The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine and at a temperature within the range of 0° to 120° C.

Compounds of formula (V) may be prepared by treatment of compounds of formula (II), in which the 4" hydroxy is suitably activated, with an amine of formula NH$_2$R$^{16}$ (VIIa). Suitable activated derivatives of the 4" hydroxy group include, for example, the carbonyl imidazole.

Compounds of formula (I) wherein m is 0 and U is —C(O)N($R^{16}$)— may be prepared by reaction of 4" hydroxy of formula (II) with a suitable activated derivative of the carboxylic acid HOC(O)C(O)N($R^{16}$)(CH$_2$)$_m$$Z^a R^{7a}$ (VIIb) followed where necessary by subsequent removal of the hydroxyl protecting group $R^2$ and conversion of the $Z^a R^{7a}$ group to $ZR^7$.

In a further embodiment of the invention, compounds of formula (I) wherein m is 1 to 5 and U is a group selected from —N($R^{16}$)—, —O—, —S—, may be prepared by reaction of compounds of formula (VII),

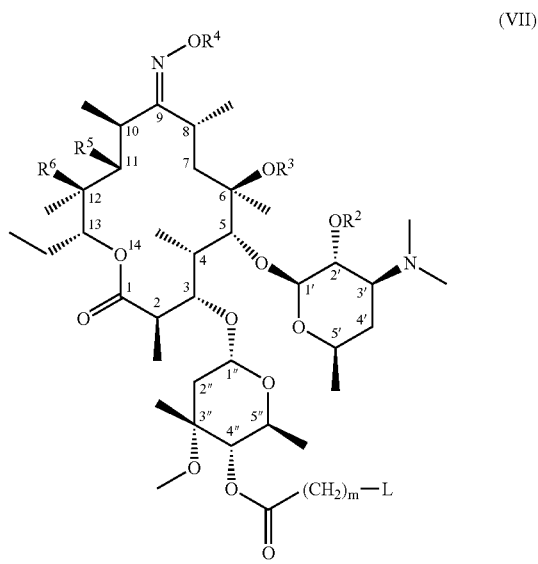

(VII)

wherein m is an integer from 1 to 5 and L is a suitable leaving group, with $X^a R^{7a}$ (IV) in which U is a group selected from —N($R^{16}$)—, —O— and —S—. The reaction is preferably carried out in a solvent such as a halohydrocarbon (e.g. dichloromethane), an ether (e.g. tetrahydrofuran, dimethoxyethane), acetonitrile or ethyl acetate and the like), dimethylsulfoxide, N,N-dimethylformamide, 1-methyl-pyrrolidone and in the presence of a base, followed, if desired, by removal of the hydroxyl protecting group $R^2$ and conversion of the $X^a R^{7a}$ group to $XR^7$. Examples of the bases which may be used include organic bases such as diisopropylethylamine, triethylamine and 1,8-diazabicyclo[5.4.0]undec-7-ene, and inorganic bases such as potassium hydroxide, cesium hydroxide, tetraalkylammonium hydroxyde, sodium hydride, potassium hydride and the like. Suitable leaving groups for this reaction include halide (e.g. chloride, bromide or iodide) or a sulfonyloxy group (e.g. tosyloxy or methansulfonyloxy).

Compounds of formula (VII) may be prepared by reaction of a compound of formula (II), wherein $R^2$ is a hydroxyl protecting group, with a suitable activated derivative of the carboxylic acid HOC(O)(CH$_2$)$_m$L (VII), wherein L is a suitable leaving group as above defined. Suitable activated derivatives of the carboxyl group are those defined above for carboxylic acid (E). The reaction is carried out using the conditions described above for the reaction of a compound of formula (I) with carboxylic acid (III).

In a preferred embodiment of the invention, compounds of formula (I) wherein m is 2, U is a group selected from —N($R^{16}$)—, —O— and —S—, may be prepared by Michael reaction of a compound of formula (IX), wherein $R^2$ is optionally a hydroxyl protecting group

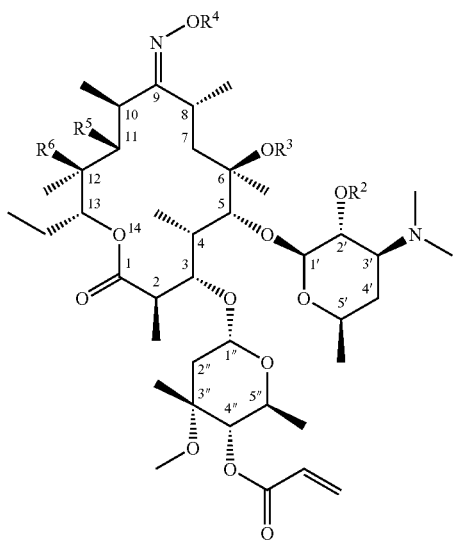

(IX)

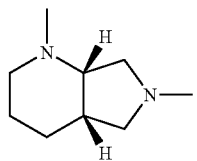

may be prepared by reaction of $X^aR^{7a}$ (IV), wherein $X^a$ has the meaning defined above with $R^{17}OC(O)(CH_2)_mL$ (X) wherein $R^{17}$ is carboxyl protecting group and L is a suitable leaving group, followed by removal of $R^{17}$.

Compounds of formula (IV) wherein X is —$U(CH_2)_sZ$- in which Z is —$N(R^{16})$—, —O— or —S—, or X is a group selected from:

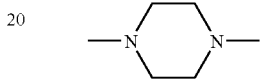 or 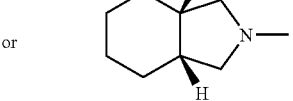

may be prepared by reaction of a compound of formula $R^{7a}L$ (XI), wherein L is a suitable leaving group such as chlorine, fluorine or bromine, with a compound of formula —$U(CH_2)_sZ$- (XII) in which Z is —$N(R^{16})$—, —O— or —S—, with piperazine or with 1H-pyrrolo[3,4-b]pyridine, octahydro.

Suitable hydroxy protecting reagents are those described by T. W. Greene and P. G. M Wuts in Protective Groups in Organic Synthesis $2^{nd}$ ed., John Wiley & Son, Inc 1991, which is incorporated by reference. Examples of suitable hydroxy protecting reagents include acetic anhydride, benzoic anhydride or a trialkylsilyl chloride in a protic solvent. Examples of aprotic solvents are dichloromethane, NN-dimethylformamide, dimethylsulfoxide, tetrahydrofuran and the like.

Suitable $R^{17}$ carboxyl protecting group include t-butyl, allyl or benzyl.

In order that the invention may be more fully understood the following examples are given by way of illustration only.

The following abbreviations are used in the text: DBU for 1,8-diazabicyclo[5.4.0]undecene-7-ene, DCM for dichloromethane, DMAP for 4-dimethylaminopyridine, DMF for N,N-dimethylformamide, EDC HCL for 1-(3-dimethylaminopropyl)-3-ethylcarbodiimide hydrochloride, DMSO for dimethyl sulfoxide, Et for ethyl, EtOH for ethanol, KO$^t$Bu for potassium tert-butoxide, Me for methyl, MeOH for methanol, i-Pr for isopropyl and i-PrOH for isopropanol.

with a compound of formula $X^aR^{7a}$ (IV). The reaction is suitably carried out in a solvent such as dimethylsulfoxide, N,N-dimethylformamide, 1-methyl-pyrrolidone, a halohydrocarbon (e.g. dichloromethane), an ether (e.g. tetrahydrofuran, dimethoxyethane), acetonitrile or ethyl acetate or alcohol (e.g methanol, isopropanol) and the like, and in the presence of a base, followed, if desired, by removal of hydroxyl protecting group $R^2$ and conversion of the $X^aR^{7a}$ group to $XR^7$.

Compounds of formula (I) may be converted into other compounds of formula (I). Thus compounds of formula (I) wherein U is —$S(O)_t$— and t is 1 or 2 may be prepared by oxidation of the corresponding compound of formula (I) wherein t is 0. The oxidation is preferably carried out using a peracid, e.g. peroxybenzoic acid, followed by treatment with a phosphine, such as triphenylphosphine. The reaction is suitably carried out in an organic solvent such as methylene chloride.

Compounds of formula (II), wherein $R^5$ or $R^6$ are hydroxy or $R^5$ and $R^6$ taken together with the intervening atoms form a cyclic group having the following structure:

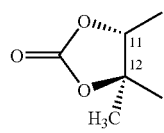

may be prepared by analogous methods to those known in the art. Thus they can be prepared according to the procedures described in EP 284 203.

Compounds of formula (III) wherein X is —$U(CH_2)_sN(R^{16})$—, in which U is —$N(R^{16})$—, —O— or —S—, or X is a group selected from:

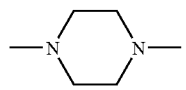

or

EXAMPLES

Intermediate 1

2'-O-Acetyl-11-O-(2-dimethylaminoethoxymethyl)-(9E)-methoximino erythromycin A

A solution of 11-O-(2-dimethylaminoethoxymethyl)-(9E)-methoximino erythromycin A$^1$ (0.423 g, 0.5 mmol) in dichloromethane (40 mL) was treated with sodium hydrogen carbonate (0.126 g, 1.5 mmol) followed by acetic anhydride (0.056 g, 0.55 mmol). After stirring overnight at room temperature the mixture was diluted with dichloromethane (10 mL) and washed with water (10 mL). The organic layer was separated, dried and evaporated to yield the title product as a solid. ESMS m/z 907 (100%) [MH$^+$].

Intermediate 2

2'-O-Acetyl-11,12-carbonate-(9E)-O-(2-propyl)oximino erythromycin A

The title compound was prepared from 11,12-carbonate-(9E)-O-(2-propyl)oximino erythromycin $A^2$ (0.6 g, 0.73 mmol) in similar fashion to that described for Intermediate 1. ESMS m/z 859 [MH$^+$].

Intermediate 3

2'-O-Acetyl-11,12-carbonate-(9E)-methoximino erythromycin A

The title compound was prepared from 11,12-carbonate-(9E)- methoximino erythromycin $A^2$ (0.615 g, 0.78 mmol) in similar fashion to that described for Intermediate 1. ESMS m/z 832 [MH$^+$].

Intermediate 4

2'-O-Acetyl-11,12-carbonate-(9E)-O-(2-pyridylmethyl)oximino erythromycin A

The title compound was prepared from 11,12-carbonate-(9E)-O-(2-pyridylmethyl)oximino erythromycin $A^3$ (0.095 g, 0.11 mmol) in similar fashion to that described for Intermediate 1. ESMS m/z 909 [MH$^+$].

Intermediate 5

2'-O-Acetyl-11,12-carbonate-(9E)-O-(methythiomethyl)oximino erythromycin A

The title compound was prepared from 11,12-carbonate-(9E)-O-(methylthiomethyl)oximino erythromycin $A^3$ (0.092 g, 0.11 mmol) in similar fashion to that described for Intermediate 1. ESMS m/z 878 [MH$^+$].

Intermediate 6

2'-O-Acetyl-11,12-carbonate-(9E)-O-(ethoxymethyl)oximino erythromycin A

The title compound was prepared from 11,12-carbonate-(9E)-O-(ethoxymethyl)oximino erythromycin $A^2$ (0.12 g, 0.14 mmol) in similar fashion to that described for Intermediate 1. ESMS m/z 876 [MH$^+$].

Intermediate 7

2'-O-Acetyl-11-O-(2-dimethylaminoethoxymethyl)-(9E)-methoximino-4''-O-propenoyl erythromycin A To a solution of Intermediate 1 (0.31 g, 0.34 mmol) in toluene (20 mL) was added triethylamine (0.069 g, 0.68 mmol) followed by 3-chloropropionyl chloride (0.052 g, 0.41 mmol) at room temperature. After stirring overnight the mixture was washed with water (10 mL), the organic layer separated, dried and evaporated to yield the title compound as a white solid. ESMS m/z 961 [MH$^+$].

Intermediate 8

2'-O-Acetyl-O-11,12-carbonate-(9E)-O-(2-propyloximino)-4-O-propenoyl erythromycin A The title compound was prepared from Intermediate 2 (0.62 g, 0.72 mmol) in similar fashion to that described for Intermediate 7.

Intermediate 9

2'-O-Acetyl-11,12-carbonate-(9E)-methoximino-4''-O-propenoyl erythromycin A

The title compound was prepared from Intermediate 3 (0.7 g, 0.84 mmol) in similar fashion to that described for Intermediate 7. ESMS m/z 886 [MH$^+$].

Intermediate 10

2'-O-Acetyl-11,12-carbonate-(9E)-O-(2-pyridylmethyloximino)-4''-O-propenoyl erythromycin A The title compound was prepared from Intermediate 4 (0.1 g, 0.11 mmol) in similar fashion to that described for Intermediate 7. ESMS m/z 963 [MH$^+$].

Intermediate 11

2'-O-Acetyl-11,12-carbonate-(9E)-O-(methythiomethyloximino)-4''-O-propenoyl erythromycin A The title compound was prepared from Intermediate 5 (0.096 g, 0.11 mmol) in similar fashion to that described for Intermediate 7. ESMS m/z 932 [MH$^+$].

Intermediate 12

2'-O-Acetyl-11,12-carbonate-(9E)-O-(ethoxymethyloximino)-4''-O-propenoyl erythromycin A The title compound was prepared from Intermediate 6 (0.12 g, 0.14 mmol) in similar fashion to that described for Intermediate 7.

Intermediate 13

6-[(2-Aminoethyl)amino]-7-chloro-1-cyclopropyl-1,4-dihydro-4-oxo-quinoline-3-carboxylic acid 7-Chloro-1-cyclopropyl-1,4-dihydro-6-fluoro4-oxo-quinoline-3-carboxylic acid (56.3 g) and ethylenediamine (36 g) were dissolved in N,N-dimethylacetamide (650 mL) at 100° C. and stirred for 8.5 h at 115° C. Water (700 mL) was added to the reaction mixture cooled at room temperature. The reaction mixture was stirred at room temperature for 2 h, cooled at 0-5° C. and stirred for 1 h. The precipitate obtained was filtered, washed with cold water, cold EtOH, and dried at 110° C. under reduced pressure for 1 h. The crude product was treated with HCl (6% aqueous solution) heating for 1 h in the presence of charcoal. After filtration, the solution was cooled to 35-40° C. and a first precipitation happened. The precipitate was filtered, washed with water and dried at 110° C. for 1 h. The title compound (6.4 g) was obtained as the hydrochloride salt. The hydrochloride salt was then converted to the free base using standard conditions.

Intermediate 14

4''-O-[3-[[2-[(3-Carboxy-7-chloro-1-cyclopropyl-1,4-dihydro-4-oxo-6-quinolinyl) amino]ethyl]amino]propionyl]-2'-O-acetyl-11-O-(2-dimethylaminoethoxymethyl)-(9E)-methoximino erythromycin A A mixture of Intermediate 7 (0.07 g, 0.07 mmol) and Intermediate 13 (0.94 g, 0.29 mmol) in DMSO (5 mL), water (10 drops) and triethylamine (0.015 g, 0.15 mmol) was heated at 80° C. After 8 h the mixture was cooled and the crude mixture chromatographed over silica gel eluting with dichloromethane containing an increasing concentration of methanol/ammonium hydroxide to yield the title compound as a white solid. ESMS m/z 1282 [MH$^+$].

Intermediate 15

4''-O-[3-[[2-[(3-Carboxy-7-chloro-1-cyclopropyl-1,4-dihydro-4-oxo-6-quinolinyl) amino]ethyl]amino]propionyl]-2'-O-acetyl-11,12-carbonate-(9E)-O-(2-propyl)oximino erythromycin A The title compound was prepared by the method of Intermediate 14 but using Intermediate 8 (0.6 g, 0.065 mmol) and Intermediate 13 (0.04 g, 0.13 mmol).

Intermediate 16

4"-O-[3-[[2-[(3-Carboxy-7-chloro-1-cyclopropyl-1,4-dihydro-4-oxo-6-quinolinyl) amino]ethyl]amino]propionyl]-2'-O-acetyl-11,12-carbonate(9E)-methoximino erythromycin A The title compound was prepared by the method of Intermediate 14 but using Intermediate 9 (0.14 g, 0.16 mmol) and Intermediate 13 (0.1 g, 0.31 mmol). ESMS m/z 1207 [MH$^+$].

Intermediate 17

4"-O-[3-[[2-[(3-Carboxy-1-cyclopropyl-1,4-dihydro-6-fluoro-4-oxo-7-quinolinyl) amino]ethyl]amino]propionyl]-2'-O-acetyl-11,12-carbonate-(9E)-methoximino erythromycin A The title compound was prepared by the method of Intermediate 14 but using Intermediate 9 (0.07 g, 0.079 mmol) and 7-[(2-aminoethyl)amino]-1-cyclopropyl-1,4-dihydro-6-fluoro-4-oxo-quinoline-3-carboxylic acid[4] (0.048 g, 0.16 mmol).

Intermediate 18

4"-O-[3-[[2-[(3-Carboxy-7-chloro-1-cyclopropyl-1,4-dihydro-4-oxo-6-quinolinyl) amino]ethyl]amino]propionyl]-2'-O-acetyl-11,12-carbonate-(9E)-O-(2-pyridylmethyl)oximino erythromycin A The title compound was prepared by the method of Intermediate 14 but using Intermediate 10 (0.095 g, 0.11 mmol) and Intermediate 13. ESMS m/z 1282 [MH$^-$].

Intermediate 19

4"-O-[3-[[2-[(3-Carboxy-7-chloro-1-cyclopropyl-1,4-dihydro-4-oxo-6-quinolinyl) amino]ethyl]amino]propionyl]-2'-O-acetyl-11,12-carbonate-(9E)-O-(methylthiomethyl)oximino erythromycin A The title compound was prepared by the method of Intermediate 14 but using Intermediate 11 (0.095 g, 0.11 mmol) and Intermediate 13. ESMS m/z 1251 [MH$^-$].

Intermediate 20

4"-O-[3-[[2-[(3-Carboxy-7-chloro-1-cyclopropyl-1,4-dihydro-4-oxo-6-quinolinyl) amino]ethyl]amino]propionyl]-2'-O-acetyl-11,12-carbonate-(9E)-O-(ethoxymethyl)oximino erythromycin A The title compound was prepared by the method of Intermediate 14 but using Intermediate 12 (0.13 g, 0.14 mmol) and Intermediate 13. ESMS m/z 1249 [MH$^-$].

Intermediate 21

2'-O-Acetyl-(9E)-O-ethyloximino erythromycin A

Acetic anhydride (43 µL, 1.1 eq) was added to a suspension of 9E-ethoxyimino erythromycin A[5] (336 mg, 0.4 mmol) in ethylacetate (10 ml). After stirring overnight at room temperature, 10 ml of water was added to the reaction and the mixture was stirred for an additional 20 min. The pH of the aqueous layer was adjusted to the pH 11 with 1N NaOH and extracted with ethylacetate. The organic layer was washed with brine, dried and evaporated to yield the title compound as a white solid (200 mg). ESMS m/z 820 [MH$^+$]

Intermediate 22

2'-O-Acetyl-(9E)-O-propyloximino erythromycin A

The title compound was prepared from (9E)-O-propyloximino erythromycin A[5] (1.87 g, 2.4 mmol) in an analogous procedure to that described for Intermediate 21. ESMS m/z 833 [MH$^+$]

Intermediate 23

2'-O-Acetyl-(9E)-O-(2-propyl)oximino erythromycin A

The title compound was prepared from (9E)-O-(2-propyl) oximino erythromycin A[5] (1.09 g, 1.3 mmol) in an analogous procedure to that described for Intermediate 21. ESMS m/z 833 [MH$^{30}$]

Intermediate 24

2'-O-Acetyl4"-O-propenoyl-(9E)-O-propyloximino erythromycin A

Intermediate 22 (2.0 g, 2.4 mmol) was dissolved in toluene (15 mL) and the solvent was evaporated. This operation was repeated twice. The residue was dissolved again in toluene (30 mL) and the solution was stirred under argon. Triethylamine (1.76 mL) was added followed by 3-chloropropionyl chloride (0.46 mL), added in two portions over a period of 10 minutes. After 0.5 h a saturated aqueous solution of NaHCO$_3$ (50 mL) was added and the aqueous phase was extracted with toluene (3×50 mL). The organic phase was concentrated under reduced pressure, the residue (2.34 g) dissolved in MeOH (350 mL) and the resulting solution stirred overnight. The solvent was evaporated under reduced pressure affording the title compound (2.0 g). MS; m/z (ES): 846.3 [MH]$^+$

Intermediate 25

2'-O-Acetyl-(9E)-O-acetyloximino erythromycin A

The title compound was prepared from (9E)-O-oximino erythromycin A[6] (2.0 g, 2.7 mmol) in similar fashion to that described for Intermediate 1. ESMS m/z 833.3 [MH$^+$]

Intermediate 26

7-Chloro-1-cyclopropyl-6-(2-hydroxy-ethoxy)-4-oxo-1,4-dihydro-quinoline3-carboxylic acid (A) and 1-Cyclopropyl-6-fluoro-7-(2-hydroxy-ethoxy)-4-oxo-1,4-dihydro-quinoline-3-carboxylic acid (B)

To a mixture of DMSO (5 ml) and ethyleneglycol (6 ml), KO$^t$Bu (1.6 g, 14.23 mmol) was added portionwise over 10 min, and then heated to 90° C. To the mixture, 7chloro-1-cyclopropyl-6-fluoro-4-oxo-1,4-dihydro-quinoline-3-carboxylic acid (1.0 g) was added portionwise over 20 min, the temperature was increased to 105° C. and the mixture was stirred for 6 h. Water (30 ml) was added to the reaction solution and the pH of the solution was adjusted to pH=5. The resulting solution was left in the refrigerator overnight. The precipitate obtained was filtered, washed with cold water, and dried affording a 2:1 mixture of Intermediate 26A and Intermediate 26B (1.0 g).

Part of the crude product (700 mg) was dissolved in EtOH (15 ml) by heating to the reflux. The resulting solution was cooled to 30° C. and a first precipitation occurred. The precipitate was filtered, washed with cold EtOH and dried under reduced pressure. Intermediate 26A (204 mg) was obtained as a white solid. $^1$H-NMR (500 MHz, DMSO-d6) δ: 15.06 (s, 1H), 8.71 (s, 1H), 8.40 (s, 1H), 7.86 (s, 1H), 4.97 (t, 1H), 4.25 (t, 2H), 3.87 (m, 1H), 3.82 (q, 2H), 1.32 (m, 2H), 1.20 (m, 2H). $^{13}$C-NMR (75 MHz, DMSO-d6) δ: 176.61, 165.67, 152.47, 147.54, 135.34, 129.48, 124.95, 120.02, 106.90, 106.66, 71.22, 59.15, 35.99, 7.46. MS; m/z (ES): [MH]$^+$

Intermediate 27

7-Chloro-6-[2-(2-cyano-ethoxy)-ethoxy]1-cyclopropyl-4-oxo-1,4-dihydro-quinoline-3-carboxylic acid To a suspension of Intermediate 26A (2 g) in acrylonitrile (40 ml) was added DBU (2.3 ml). The reaction mixture was stirred at 80° C. for 24 h. The acrylonitrile was evaporated under reduced pressure. Isopropanol (30 ml) was added to the residue and the pH of the solution was adjusted to pH=5 by adding 2M HCl, during which the product precipitated. The precipitate was filtered, washed with water, and dried affording Intermediate 27 (1.7 g) as a white solid. $^1$H-NMR (500 MHz, DMSO-d6) δ: 8.68 (s, 1H), 8.38 (s, 1H), 7.84 (s, 1H), 4.38 (t, 2H), 3.91 (t, 2H), 3.86 (m, 1H), 3.75 (t, 2H), 2.79 (t, 2H), 1.32 (m, 2H), 1.20 (m, 2H). $^{13}$C-NMR (75 MHz, DMSO-d6) δ: 176.63, 165.65, 152.18, 147.61, 135.50, 129.44, 124.97, 120.04, 119.11, 106.96, 106.80, 69.02, 68.30, 65.49, 35.99, 18.06, 7.46. MS; m/z (ES): 377.03 [MH]$^+$ Intermediate 28

6-[2-(2-Carboxy-ethoxy)-ethoxy]-7-chloro-1-cyclopropyl-4-oxo-1,4-dihydro-quinoline-3-carboxylic acid A solution of Intermediate 27 (1.10 g) in a mixture of conc. $H_2SO_4$ (10 ml) and $H_2O$ (20 ml) was stirred at 75° C. for 24 h. The pH of the reaction mixture was adjusted to 0.2 with 40% NaOH, during which the product precipitated. The precipitate was filtered, washed with water, and dried affording Intermediate 28 (0.8 g) as a white solid. $^1$H-NMR (300 MHz, DMSO-d6) δ: 15.0 (s, 1H), 11.8 (s, 1H), 8.69 (s, 1H), 8.38 (s, 1H), 7.85 (s, 1H), 4.35 (m, 2H), 3.91-3.82 (m, 3H), 3.74 (dt, 2H), 2.49 (m, 2H), 1.31 (m, 2H), 1.19 (m, 2H). MS; m/z (ES): 396.02 [MH]$^+$.

Intermediate 29

7-Chloro-1-cyclopropyl-6-(2-hydroxy-ethylamino)-4-oxo-1,4-dihydro-quinoline-3-carboxylic acid (A) and 1-Cyclopropyl-6-fluoro-7-(2-hydroxy-ethylamino)-4-oxo-1,4-dihydro-quinoline-3-carboxylic acid (B)

To a solution of ethanolamine (55.5 ml) in N-methyl pyrrolidinone (500 ml) at 95° C., 7-chloro-1-cyclopropyl-6-fluoro-4-oxo-1,4-dihydro-quinoline-3-carboxylic acid (50.0 g) was slowly added under vigorous stirring. The temperature was increased to 105° C. and the reaction mixture was stirred at this temperature for 22 hours. The reaction mixture was cooled to about 60° C. and poured into MeOH (800 ml). This mixture was stirred in an ice bath and the precipitate was filtered off and dried affording a mixture of Intermediate 29A and Intermediate 29B (49 g ) in a 1:1 ratio.

Intermediate 29A: MS; m/z (ES): 322.99 [MH]$^+$
Intermediate 29B: MS; m/z (ES): 307.02 [MH]$^+$ Intermediate 30

7-Chloro-6-[2-(2-cyano-ethoxy)-ethylamino]-1-cyclopropyl-4-oxo-1,4-dihydro-quinoline-3-carboxylic acid (A) and 7-[2-(2-Cyano-ethoxy)-ethylamino]-1-cyclopropyl-6-fluoro-4-oxo-1,4-dihydro-quinoline-3-carboxylic acid (B)

A solution of a mixture of Intermediate 29A and Intermediate 29B (14 g) in acrylonitrile (140 ml) and DBU (14 ml) was stirred at 70° C. for 16 hours. The solvent was evaporated and the residue dissolved in i-PrOH (50 ml). Water (50 ml) was added and the pH value adjusted to 4. The precipitate was filtered and then triturated with methanol. After filtration, 5.35 g of pure Intermediate 30A was obtained. The mother liquor was left overnight at 4° C. and 4.4 g of Intermediate 30B precipitated.

Intermediate 30A: $^1$H-NMR (500 MHz, DMSO-d6) δ: 8.56 (s, 1H), 8.23 (s, 1H), 7.40 (s, 1H), 5.93 (t, NH), 3.83 (qv, 1H), 3.72 (t, 2H), 3.67 (t, 2H), 3.46 (q, 2H), 2.79 (t, 2H), 1.30 (q, 2H), 1.18 (q, 2H). $^{13}$C-NMR (75 MHz, DMSO-d6) δ: 176.52, 166.09, 145.72, 142.72, 132.17, 126.37, 125.38, 119.15, 118.99, 106.14, 102.76, 67.93, 65.05, 42.40, 35.77, 18.01, 7.32. MS; m/z (ES): 376.02 [MH]$^+$ Intermediate 30B: $^1$H-NMR (500 MHz, DMSO-d6) δ: 8.55 (s, 1H), 7.76 (d, 1H), 7.22 (d, 1H), 3.74 (t, 2H+1H), 3.67 (t, 2H), 3.52 (q, 2H), 2.78 (t, 2H), 1.31 (m, 2H), 1.18 (m, 2H). $^{13}$C-NMR (75 MHz, DMSO-d6) δ: 175.80, 166.20, 148.12, 146.89, 142.55, 140.30, 119.22, 108.79, 106.10, 96.68, 68.29, 65.17, 42.06, 35.70, 17.99, 7.48. MS; m/z (ES): 360.04 [MH]$^+$ Intermediate 31

6-[2-(2-Carboxy-ethoxy)-ethylamino]-7-chloro-1-cyclopropyl-4-oxo-1,4-dihydro-quinoline-3-carboxylic acid A solution of Intermediate 30A (4.7 g) in 60 ml conc. $H_2SO_4$ and 60 ml $H_2O$ was stirred for 20 hours at 75° C. The reaction mixture was poured into water (150 ml) and the pH value was adjusted to 2. Filtration of the precipitate obtained yielded pure Intermediate 31 (3.07 g); $^1$H-NMR (500 MHz, DMSO-d6) δ: 8.56 (s, 1H), 8.23 (s, 1H), 7.39 (s, 1H), 3.82 (m, 1IH), 3.66 (q, 2H+2H), 3.42 (t, 2H), 2.49 (t, 2H), 1.30 (q, 2H), 1.17 (m, 2H). $^{13}$C-NMR (75 MHz, DMSO-d6) δ: 178.70, 174.73, 168.28, 147.89, 144.93, 134.34, 128.55, 127.56, 121.15, 118.99, 108.32, 104.90, 69.98, 68.16, 44.59, 37.95, 36.74, 9.50. MS; m/z (ES): 395.05 [MH]$^+$.

The compounds of Examples 1 to 15 were prepared by the procedures described below.

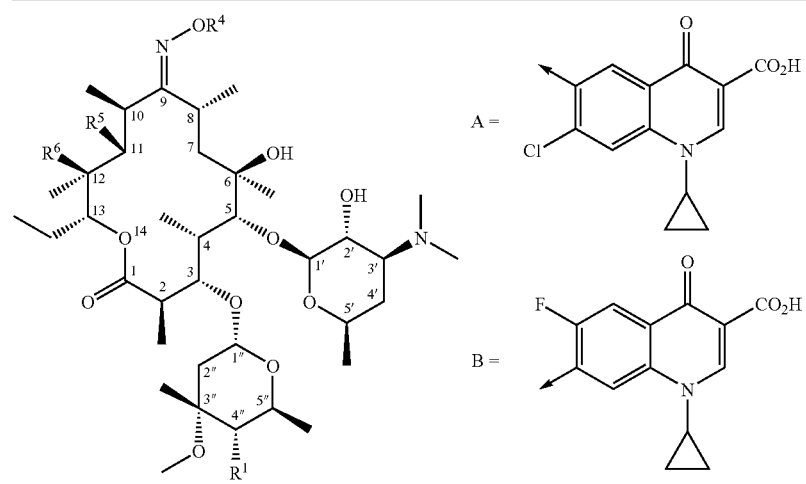

| Example | R$^1$ | R$^4$ | R$_5$ | R$_6$ |
|---|---|---|---|---|
| 1 | OC(O)(CH$_2$)$_2$N(H)(CH$_2$)$_2$NHA | Me | OCH$_2$O(CH$_2$)$_2$NMe$_2$ | OH |
| 2 | OC(O)(CH$_2$)$_2$N(H)(CH$_2$)$_2$NHA | i-Pr | R$_5$R$_6$ —O—C(O)—O— | |
| 3 | OC(O)(CH$_2$)$_2$N(H)(CH$_2$)$_2$NHA | Me | R$_5$R$_6$ —O—C(O)—O— | |
| 4 | OC(O)(CH$_2$)$_2$N(H)(CH$_2$)$_2$NHB | Me | R$_5$R$_5$ —O—C(O)—O— | |
| 5 | OC(O)(CH$_2$)$_2$N(H)(CH$_2$)$_2$NHB | i-Pr | R$_5$R$_6$ —O—C(O)—O— | |
| 6 | OC(O)(CH$_2$)$_2$N(H)(CH$_2$)$_2$NHA | 2-pyridylCH$_2$ | R$_5$H$_6$ —O—C(O)—O— | |
| 7 | OC(O)(CH$_2$)$_2$N(H)(CH$_2$)$_2$NHA | MeSCH$_2$ | R$_5$R$_6$ —O—C(O)—O— | |
| 8 | OC(O)(CH$_2$)$_2$N(H)(CH$_2$)$_2$NHA | EtOCH$_2$ | R$_5$R$_6$ —O—C(O)—O— | |

| | -continued | | | |
|---|---|---|---|---|
| 9 | OC(O)(CH₂)₂O(CH₂)₂OA | Et | OH | OH |
| 10 | OC(O)(CH₂)₂O(CH₂)₂OA | Pr | OH | OH |
| 11 | OC(O)(CH₂)₂O(CH₂)₂OA | i-Pr | OH | OH |
| 12 | OC(O)(CH₂)₂O(CH₂)₂NHA | Et | OH | OH |
| 13 | OC(O)(CH₂)₂O(CH₂)₂NHA | Pr | OH | OH |
| 14 | OC(O)(CH₂)₂N(H)(CH₂)₂NHA | Pr | OH | OH |
| 15 | OC(O)(CH₂)₂O(CH₂)₂OA | H | OH | OH |

Example 1

4"-O-[3-[[2-[(3-Carboxy-7-chloro-1-cyclopropyl-1,4-dihydro-4-oxo-6-quinolinyl) amino]ethyl]amino]propionyl]-11-O-(2-dimethylaminoethoxymethyl)-(9E)-methoximino erythromycin A A solution of Intermediate 14 (0.03 g, 0.023 mmol) in methanol (3 mL) was warmed at 50° C. with stirring. After 16 h the mixture was cooled and the solvent evaporated to yield the title compound as a yellow solid. ESMS m/z 1240 [MH⁺]. $C^{13}$ NMR δ CDCl₃ 7.50, 9.20, 10.9, 13.6, 14.2, 17.4, 17.6, 18.2, 20.8, 21.2, 22.6, 23.9, 27.1, 31.2, 34.3, 34.6, 34.9, 35.7, 39.3, 39.9, 41.9, 43.0, 44.3, 44.7, 44.8, 47.5, 49.1, 58.8, 60.3, 63.5, 64.7, 66.8, 68.1, 71.5, 73.2, 74.4, 76.3, 77.6, 78.6, 78.8, 79.0, 84.4, 96.2, 98.9, 102.4, 104.1, 110.1, 118.9, 127.0, 127.4, 133.1, 143.4, 146.3, 167.4, 169.9, 172.5, 176.6, 177.2.

Example 2

4"-O-[3-[[2-[(3-Carboxy-7-chloro-1-cyclopropyl-1,4-dihydro-4-oxo-6-quinolinyl) amino]ethyl]amino]propionyl]-11,12-carbonate-(9E)-O-(2-propyl)oximino erythromycin A In an analogous procedure to that of Example 1, Intermediate 15 gave the title compound as a white solid. ESMS m/z 1192 [MH⁺].

Example 3

4"-O-[3-[[2-[(3-Carboxy-7-chloro-1-cyclopropyl-1,4-dihydro-4-oxo-6-quinolinyl) amino]ethyl]amino]propionyl]-11,12-carbonate-(9E)-methoximino erythromycin A In an analogous procedure to that of Example 1, Intermediate 16 gave the title compound as a white solid. ESMS m/z 1165 [MH⁺].

Example 4

4"-O-[3-[[2-[(3-Carboxy-1-cyclopropyl-1,4-dihydro-6-fluoro-4-oxo-7-quinolinyl) amino]ethyl]amino]propionyl]-11,12-carbonate-(9E)-methoximino erythromycin A In analogous procedure to that of Example 1, Intermediate 17 gave the title compound as a white solid; ¹H NMR δ (CD₃OD) inter alia 8.78 (1H, s), 7.87(1H, d, J=11.6 Hz), 7.35 (1H, d, J=6.0 Hz).

Example 5

4"-O-[3-[[2-[(3-Carboxy-1-cyclopropyl-1,4-dihydro-6-fluoro-4-oxo-7-quinolinyl) amino]ethyl]amino]propionyl]-11,12-carbonate(9E)-O-(2-propyl)oximino erythromycin A A mixture of Intermediate 8 (0.06 g, 0.066 mmol) and 7-[(2-aminoethyl)amino]-1-cyclopropyl-1,4-dihydro-6-fluoro-4-oxo-quinoline-3-carboxylic acid[4] (0.04 g, 0.13 mmol) in DMSO (3 mL) and diethylisopropylamine (0.029 mL, 0.17 mmol) was heated at 80° C. for 8 h. After stirring at room temperature for 12 h the mixture was diluted with diethyl ether and the solid formed filtered to yield the title compound as a white solid. ESMS m/z 1176 [MH⁺].

Example 6

4"-O-[3-[[2-[(3-Carboxy-7-chloro-1-cyclopropyl-1,4-dihydro-4-oxo-6-quinolinyl) amino]ethyl]amino]propionyl]-11,12-carbonate-(9E)-O-(2-pyridylmethyl)oximino erythromycin A In an analogous procedure to that of Example 1, Intermediate 18 gave the title compound as a white solid. ESMS m/z 1240 [M-H]⁻.

Example 7

4"-O-[3-[[2-[(3-Carboxy-7-chloro-1-cyclopropyl-1,4-dihydro-4-oxo-6-quinolinyl) amino]ethyl]amino]propionyl]-11,12-carbonate-(9E)-O-(methylthiomethyl)oximino erythromycin A In an analogous procedure to that of Example 1, Intermediate 19 gave the title compound as a white solid. ESMS m/z 1210 [M-H]⁻.

Example 8

4"-O-[3-[[2-[(3-Carboxy-7-chloro-1-cyclopropyl-1,4-dihydro-4-oxo-6-quinolinyl) amino]ethyl]amino]propionyl]-11,12-carbonate-(9E)-O-(ethoxymethyl)oximino erythromycin A In an analogous procedure to that that of Example 1, Intermediate 20 gave the title compound as a white solid. ESMS m/z 1207 [M-H]⁻.

Example 9

4"-O-[3-[[2-[(3-Carboxy-7-chloro-1-cyclopropyl-1,4-dihydro-4-oxo-6-quinolinyl)-oxy]ethyl]oxy]propionyl]-(9E)-O-ethyloximino erythromycin A EDC HCl (105 mg, 0.49 mol) was added to a DMF/dry (1 ml) solution of Intermediate 28 (130 mg, 0.33 mmol) cooled on ice bath and the reaction mixture was stirred at 0° C. for ~30 min under the flow of N₂. A solution of Intermediate 21 (200 mg, 0.25 mmol) in 0.5 ml DMF was added and after 1 hour DMAP (50 mg; 0.33 mmol) was also added. The resulting mixture was stirred for 24 h, during which time the reaction mixture was allowed to warm to ambient temperature. Water (10 ml) and DCM (15 ml) were added and the layers separated. The water layer was extracted twice with DCM. The organic layers are collected, dried on Na₂SO₄, filtered off and the organic solvent evaporated. The oily residue (260 mg) was dissolved in MeOH (20 ml) and the solution was stirred overnight. The solution was then heated for 2 h on an oil bath at 60° C. The methanol was evaporated under vacuum and the foamy residue purified by column chromatography (DCM:MeOH:NH$_3$=90:9:1.5) yielding the title compound (20 mg). ESMS m/z 1155 90% [MH$^+$]. C$^{13}$ NMR δ CDCl$_3$ 177.5, 174.6, 171.4, 171.1, 166.8, 153.2, 147.3, 135.6, 131.3, 125.8, 119.3, 108.3, 107.7, 100.6, 95.9, 83.2, 78.9, 78.5, 77.0, 74.9, 74.2, 72.9, 71.3, 70.7, 69.6, 69.5, 69.2, 67.1, 66.9, 65.4, 63.0, 49.4,44.5, 38.2, 37.7, 35.6, 35.2, 32.9, 29.7, 26.9, 26.3, 21.2, 21.1, 20.9, 18.6, 18.1, 16.3, 14.4, 10.6, 9.9, 8.3.

Example 10

4"-O-[3-[[2-[(3-Carboxy-7-chloro-1-cyclopropyl-1,4-dihydro-4-oxo-6-quinolinyl)-oxy]ethyl]oxy]propionyl]-(9E)-O-propyloximino erythromycin A In an analogous procedure to that of Example 9, Intermediate 22 gave the title compound as a yellow solid. ESMS m/z 1168 90%[MH$^+$]. C$^{13}$ NMR δ CDCl$_3$ 177.5, 174.7, 171.3, 171.0, 166.8, 153.1, 147.3, 135.5, 131.3, 125.7, 119.2, 108.3, 107.7, 101.0, 95.9, 82.9, 79.0, 78.6, 77.0, 75.7, 74.9, 74.2, 72.9, 71.2, 70.7, 69.4, 69.2, 67.1, 65.3, 62.9, 49.4, 44.5, 38.2, 37.6, 35.6, 35.2, 32.8, 26.9, 26.2, 22.3, 21.3, 20.9, 18.7, 18.1, 16.3, 14.5, 10.6, 10.4, 8.3.

Example 11

4"-O-[3-[[2-[(3-Carboxy-7-chloro-1-cyclopropyl-1,4-dihydro-4-oxo-6-quinolinyl)-oxy]ethyl]oxy]propionyl]-(9E)-O-(2-propyl)oximino erythromycin A In an analogous procedure to that of Example 9, Intermediate 23 gave the title compound as a yellow solid. ESMS m/z 1169 80% [MH$^+$]. C$^{13}$ NMR δ CDCl$_3$ 177.5, 174.9, 171.2, 171.0, 166.7, 153.1, 147.3, 135.5, 131.2, 125.8, 119.2, 108.4, 107.7, 101.6, 96.1, 82.7, 79.3, 78.8, 76.9, 75.4, 75.1, 74.2, 72.8, 71.2, 70.8, 69.4, 69.1, 67.6, 67.1, 65.3, 62.9, 49.5, 44.6, 38.5, 37.7, 35.5, 35.4, 35.2, 32.8, 29.7, 26.9, 26.4, 21.7, 21.6, 21.5, 21.1, 21.0, 18.6, 18.2, 16.3, 14.4, 10.6, 9.5, 8.3.

Example 12

4"-O-[3-[[2-[(3-Carboxy-7-chloro-1-cyclopropyl-1,4-dihydro-4-oxo-6-quinolinyl)-amino]ethyl]oxy]propionyl]-(9E)-O-ethyloximino erythromycin A EDC HCl (660 mg, 3.45 mol) was added to a DMF/dry (4 ml) solution of Intermediate 31 (904 mg, 2.3 mmol) cooled on ice bath and the reaction mixture was stirred at 0° C. for ~30 min under the flow of N$_2$. A solution of Intermediate 21 (1.5 g, 1.8 mmol) in 4 ml of DCM was then added and after 1 hour DMAP (300 mg, 2.45 mmol) was also added. The resulting mixture was stirred for 24 h, during which time the reaction mixture was allowed to warm to ambient temperature. Water (10 ml) and DCM (15 ml) were added and the layers separated. The water layer was extracted twice with DCM. The organic layers were collected, dried on Na$_2$SO$_4$, filtered off and the organic solvent evaporated. The residue was dissolved in MeOH (50 ml) and the solution was stirred overnight at 60° C. on an oil bath. The methanol was evaporated under vacuum and the foamy residue was purified by column chromatography (DCM:MeOH:NH$_3$=90:9: 1.5) yielding the title compound (120 mg). ESMS m/z 1153 80% [MH$^+$]. C$^{13}$ NMR δ CDCl$_3$177.5, 174.9, 171.3, 171.2, 167.3, 145.9, 142.9, 132.7, 127.6, 126.3, 118.1, 107.6, 104.5, 101.7, 96.1, 82.7, 79.3, 76.9, 75.2, 74.2, 72.8, 71.1, 70.7, 69.5, 68.8, 67.6, 66.3, 65.3, 62.9, 49.5, 44.5, 43.3, 40.4, 38.6, 37.7, 35.4, 35.3, 34.9, 32.8, 29.7, 26.9, 26.4, 21.6, 21.1, 21.0, 18.6, 18.2, 16.3, 14.4, 14.1, 10.7, 9.5, 8.1.

Example 13

4"-O-[3-[[2-[(3-Carboxy-7-chloro-1-cyclopropyl-1,4-dihydro-4-oxo-6-quinolinyl)-amino]ethyl]oxy]propionyl]-(9E)-O-propyloximino erythromycin A In an analogous procedure to that of Example 12, Intermediate 22 gave the title compound as a yellow solid. ESMS m/z 1167 [MH$^+$]. C$^{13}$ NMR δ CDCl$_3$ 176.9, 174.4, 170.6, 166.8, 145.4, 142.3, 132.1, 127.0, 125.7, 117.5, 107.0, 103.9, 100.9, 95.5, 82.2, 79.6, 78.7, 76.3, 75.0, 74.5, 73.6, 72.2, 70.5, 70.1, 68.2, 66.8, 65.7, 64.7, 62.3, 49.2, 43.9, 42.7, 39.9, 37.9, 37.0, 34.8, 34.7, 34.4, 32.2, 29.1, 26.4, 25.7, 21.7, 20.9, 20.5, 20.4, 18.1, 17.5, 15.6, 14.3, 10.5, 10.1, 8.9, 7.5.

Example 14

4"-O-[3-[[2-[(3-Carboxy-7-chloro-1-cyclopropyl-1,4-dihydro-4-oxo-6-quinolinyl)-amino]ethyl]amino]propionyl]-(9E)-O-propyloximino erythromycin A Intermediate 13 (1.3 g) was added to a solution of Intermediate 24 (1.1 g, 1.3 mmol) in CH$_3$OH (20 mL). The resulting mixture was heated at 70° C. for 48 h. The solvent was concentrated under reduced pressure and the residue purified by silica column (CHCl$_3$/MeOH/NH$_4$OH (6:1:0.1)) affording the title compound (120 mg). MS; m/z (ES): 1166.6 [MH]$^+$. C$^{13}$ NMR δ CDCl$_3$ 177.5, 175.0, 174.9, 172.0, 171.2, 167.3, 145.9, 143.1, 132.6, 127.7, 126.9, 126.3, 118.1, 107.6, 104.5, 101.7, 96.1, 82.9, 79.5, 78.8, 76.9, 75.6, 75.4, 75.2, 74.2, 72.8, 71.1, 70.7, 67.6, 65.3, 63.0, 49.5, 47.5, 44.6, 44.4, 42.7, 40.4, 38.6, 37.7, 35.4, 34.9,32.9, 29.7, 27.0, 26.3, 22.3, 21.6, 21.2, 21.1, 18.7, 18.2, 16.3, 14.5, 10.7, 10.4, 9.5, 8.4.

Example 15

4"-O-[3-[[2-[(3-Carboxy-7-chloro-1-cyclopropyl-1,4-dihydro-4-oxo-6-quinolinyl)-oxygen]ethyl]oxygen]propionyl]-(9E)-oximino erythromycin A In an analogous procedure to that of Example 9, Intermediate 25 (0.5 g, 0.6 mmol) gave the title compound. The residue was purified by column chromatography (DCM-MeOH-NH$_4$OH=90:9:1.5). ESMS m/z 1126.4 [MH$^+$].

REFERENCES

1. Knowles et al., *J. Antibiot.*, 1989, 42, 454-62.
2. Hunt et al., *J. Antibiot.*, 1989, 42, 1817-22.
3. EP 284203, 1988.
4. Yoshida et al *J. Pharm. Soc. Japan*, 1990, 110, 258.
5. Compound was prepared by the procedure described in EP 1 167 375 (page 72) starting from erythromycin oxime.
6. Tetrahedron Lett., 1967: 1645, 1967.

Biological Data

The MIC (μg/ml) of test compounds against various organisms was determined including: *S. aureus* Smith ATCC 13709, *S. pneumoniae* SP030, *S. pyogenes* 3565, *E. faecalis* ATCC 29212, *H. influenzae* ATCC 49247, *M. catarrhalis* ATCC 23246.

Examples 1-3 and 6-8 have an MIC≦1 μg/ml against *S. aureus* Smith ATCC 13709, *S. pneumoniae* SPO30, *S. pyogenes* 3565 and *E. faecalis* ATCC 29212.

Examples 1 and 3 have an MIC≦2 µg/ml against *H. influenzae* ATCC 49247 and *M. catarrhalis* ATCC 23246.

Examples 1-3 and 6-8 have an MIC<0.25 µg/ml against erythromycin resistant strains of *Streptococcus pneumoniae* and *Streptococcus pyogenes*.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I)

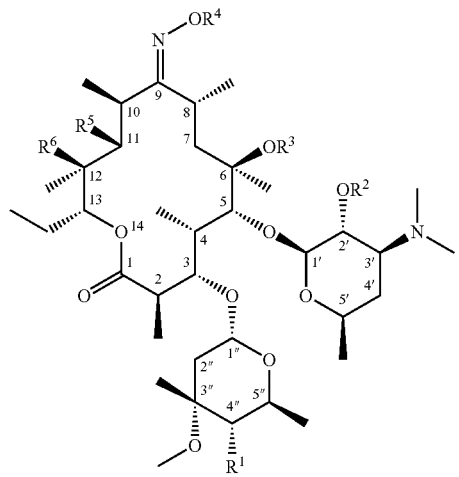

(I)

wherein
- $R^1$ is $OC(O)(CH_2)_m XR^7$;
- $R^2$ is hydrogen or a hydroxyl protecting group;
- $R^3$ is hydrogen, $C_{1-4}$alkyl or $C_{3-6}$alkenyl optionally substituted by 9 to 10 membered fused bicyclic heteroaryl;
- $R^4$ is hydrogen, $C_{1-4}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, $OR^8$, $S(O)_n R^8$, $NR^8R^9$, $CONR^8R^9$, halogen and cyano;
- $R^5$ is hydroxy, $C_{3-6}$alkenyloxy optionally substituted by 9 to 10 membered fused bicyclic heteroaryl, or $O(CH_2)_p O(CH_2)_q R^{10}$,
- $R^6$ is hydroxy, or
- $R^5$ and $R^6$ taken together with the intervening atoms form a cyclic group having the following structure:

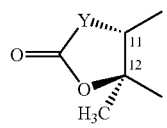

wherein Y is a bivalent radical selected from $-CH_2-$, $-CH(CN)-$, $-O-$, $-N(R^{11})-$ and $-CH(SR^{11})-$;

$R^7$ is a heterocyclic group having the following structure:

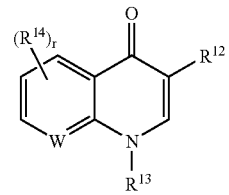

or

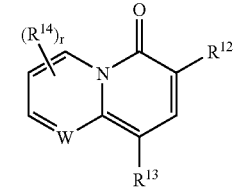

- $R^8$ and $R^9$ are each independently selected from hydrogen and $C_{1-4}$alkyl;
- $R^{10}$ is hydrogen or $NR^8R^9$;
- $R^{11}$ is hydrogen or $C_{1-4}$alkyl substituted by a group selected from optionally substituted phenyl, optionally substituted 5 or 6 membered heteroaryl and optionally substituted 9 to 10 membered fused bicyclic heteroaryl;
- $R^{12}$ is hydrogen, $C(O)OR^{15}$, $C(O)NHR^{15}$ or $C(O)CH_2NO_2$;
- $R^{13}$ is $C_{1-4}$alkyl optionally substituted by hydroxy or $C_{1-4}$alkoxy, $C_{3-7}$cycloalkyl, or optionally substituted phenyl or benzyl;
- $R^{14}$ is halogen, $C_{1-4}$alkyl, $C_{1-4}$thioalkyl, $C_{1-4}$alkoxy, $NH_2$, $NH(C_{1-4}alkyl)$ or $N(C_{1-4}alkyl)_2$;
- $R^{15}$ is hydrogen or $C_{1-4}$alkyl optionally substituted by up to three groups independently selected from halogen, $C_{1-4}$alkoxy, $OC(O)C_{1-4}$alkyl and $OC(O)OC_{14}$alkyl;
- $R^{16}$ is hydrogen, $C_{1-4}$alkyl, $C_{3-7}$cycloalkyl, optionally substituted phenyl or benzyl, acetyl or benzoyl;
- $R^{17}$ is hydrogen or $R^{14}$, or $R^{17}$ and $R^{13}$ are linked to form the bivalent radical $-O(CH_2)_2-$ or $-(CH_2)_v-$;
- X is $-U(CH_2)_s Z-$ or X is a group selected from:

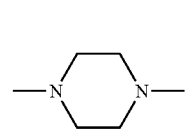 and 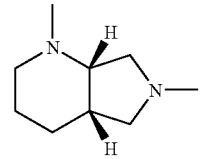

- U and Z independently are a divalent radical selected from $-N(R^{16})-$, $-O-$, $-S(O)_t-$, $-N(R^{16})C(O)-$, $-C(O)N(R^{16})-$ and $-N[C(O)R^{16}]-$;
- W is $CR^{17}$ or a nitrogen atom;
- m is 0 or an integer from 1 to 5;
- n, r and t are each independently selected from 0, 1 and 2;
- p and q are each independently selected from 1 to 6;
- s is an integer from 2 to 8; and
- v is 2 or 3;

or a pharmaceutically acceptable salt thereof.

2. A compound according to claim 1 wherein $R^2$ is hydrogen; or a pharmaceutically acceptable salt thereof.

3. A compound according to claim 1 wherein $R^3$ is hydrogen; or a pharmaceutically acceptable salt thereof.

4. A compound according to claim 3 wherein $R^4$ is hydrogen or $C_{1-4}$alkyl optionally substituted by up to three substituents independently selected from optionally substituted 5 or 6 membered heteroaryl, $OR^8$, $S(O)_nR^8$, $NR^8R^9$, halogen and cyano; or a pharmaceutically acceptable salt thereof.

5. A compound according to claim 4 wherein $R^5$ is hydroxy or $O(CH_2)_pO(CH_2)_qR^{10}$ and $R^6$ is hydroxy, or $R^5$ and $R^6$ taken together with the intervening atoms form a cyclic group having the following structure:

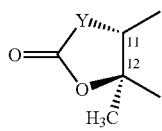

wherein Y is the bivalent radical —O—; or a pharmaceutically acceptable salt thereof.

6. A compound according to claim 5 wherein $R^7$ is a heterocyclic group having the following structure:

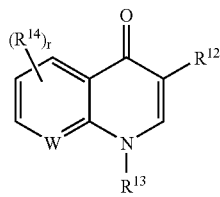

wherein W is $CR^{17}$ where $R^{17}$ is hydrogen: or a pharmaceutically acceptable salt thereof.

7. A compound according to claim 6 wherein X is —U(CH$_2$)$_s$Z- wherein U and Z are independently —NH— or —O—; or a pharmaceutically acceptable salt thereof.

8. A compound selected from:
4'-O-[3-[[2-[(3-carboxy-7-chloro-1-cyclopropyl-1,4-dihydro-4-oxo-6-quinolinyl) amino]ethyl]amino]propionyl]-11-O-(2-dimethylaminoethoxymethyl)-(9E)-methoximino erythromycin A, 4'-O-[3-[[2-[(3-carboxy-7-chloro-1-cyclopropyl-1,4-dihydro-4-oxo-6-quinolinyl) amino]ethyl]amino]propionyl]-11,12-carbonate-(9E)-O-(2-propyl)oximino erythromycin A, 4'-O-[3-[[2-[(3-carboxy-7-chloro-1-cyclopropyl-1,4-dihydro-4-oxo-6-quinolinyl) amino]ethyl]amino]propionyl]-11,12-carbonate-(9E)-methoximino erythromycin A, and 4'-O-[3-[[2-[(3-carboxy-7-chloro-1-cyclopropyl-1,4-dihydro-4-oxo-6-quinolinyl) amino]ethyl]amino]propionyl]-11,12-carbonate-(9E)-O-(ethoxymethyl)oximino erythromycin A, or a pharmaceutically acceptable salt thereof.

9. A process for the preparation of a compound as claimed in claim 1 which comprises:

a) reacting a compound of formula (II)

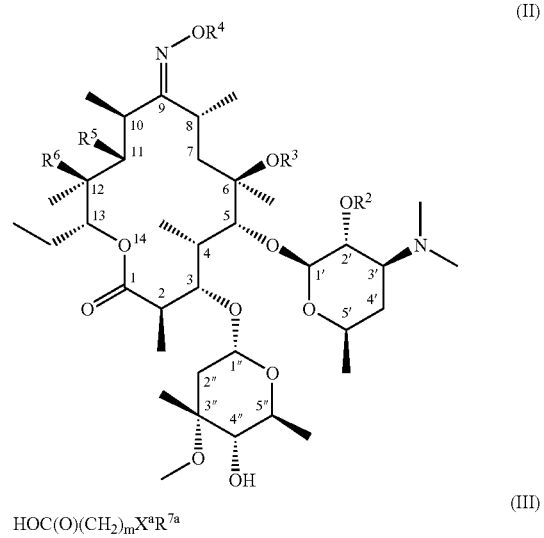

HOC(O)(CH$_2$)$_m$X$^a$R$^{7a}$ with a suitable activated derivative of the acid (III), wherein m is an integer 1 to 5, $X^a$ and $R^{7a}$ are X and $R^7$ as defined in claim 1 or protected forms of X and $R^7$, to produce a compound of formula (I) wherein m is an integer 1 to 5;

b) reacting a compound of formula (II), in which the 4' hydroxy is suitably activated, with a compound of formula $X^aR^{7a}$ (IV), wherein $R^{7a}$ is $R^{7a}$ as defined in claim 1 or a protected form of $R^7$, s and Z have the meanings defined in claim 1 and $X^a$ is —U(CH$_2$)$_s$Z— or a protected form of —U(CH$_2$)$_s$Z—, in which U is a group selected from —N(R$^{16}$)—, —O—, and —S—, to produce a compound of formula (I) wherein m is 0 and U is a group selected from —N(R$^{16}$)—, —O— and —S—;

c) reacting a compound of formula (V)

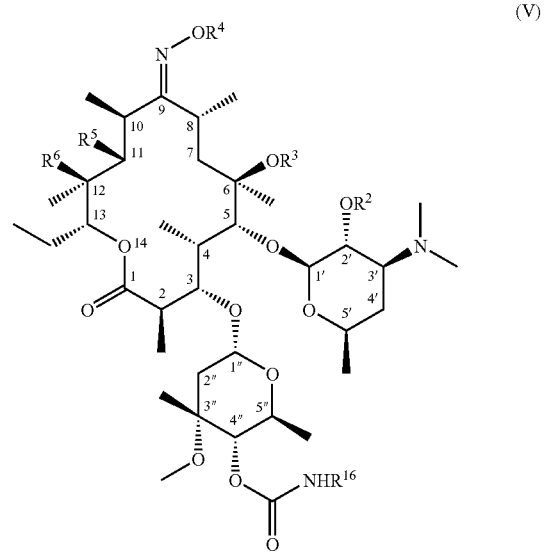

wherein $R^{16}$ has the meaning defined in claim 1 with a suitable activated derivative of the carboxylic acid HOC(O)(CH$^2$)$_s$Z$^a$R$^{7a}$ (VI), wherein $R^{7a}$ and $Z^a$ are $R^7$ and Z as defined in claim 1 or protected forms of $R^7$ and Z, to produce a compound of formula (I) wherein m is O and U is —N($R^{16}$)C(O)—;

d) reacting a compound of formula (II) with a suitably activated derivative of the carboxylic acid HOC(O)C(O)N($R^{16}$)(CH$_2$)$_s$Z$^a$R$^{7a}$ (VIIb) to produce a compound of formula (I) wherein m is O and U is —C(O)N($R^{16}$)—;

e) reacting a compound of formula (VII)

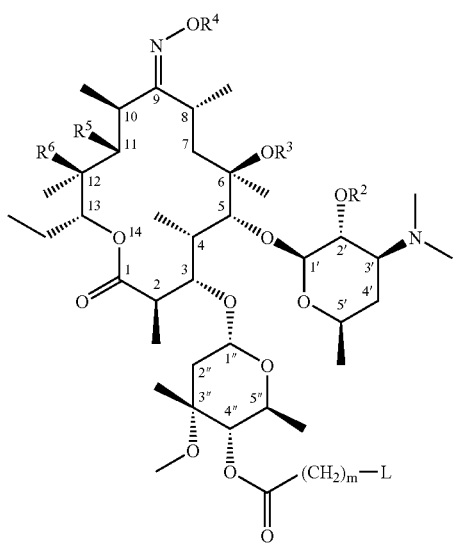

(VII)

with a compound of formula $X^aR^{7a}$ (IV), wherein $R^{7a}$ and $X^a$ are $R^7$ and X as defined in claim 1 or protected forms of $R^7$ and X, U is a group selected from —N($R^{16}$)—, —O— and —S—, and L is suitable leaving group, to produce a compound of formula (I) wherein m is 1 to 5 and U is a group selected from —N($R^{16}$)—, —O— and —S—; or f) reacting a compound of formula (IX), with a compound of formula $X^aR^{7a}$ (IV),

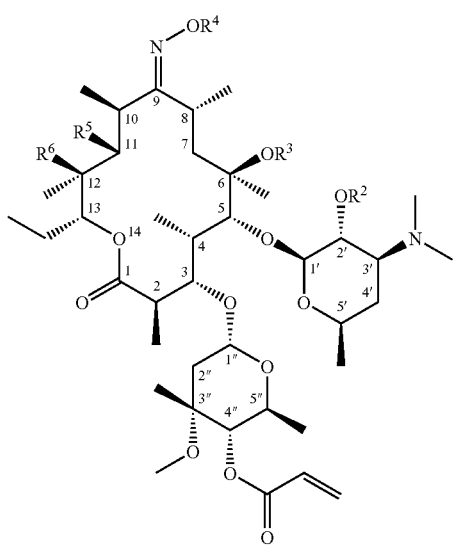

(IX)

wherein $R^{7a}$ and $X^a$ are $R^7$ and X as defined in claim 1 or protected forms of $R^7$ and X, U is a group selected from —N($R^{16}$)—, —O— and —S—, to produce a compound of formula (I) wherein m is 2 and U is a group selected from —N($R^{16}$)—, —O— and —S—;

and thereafter, if required, subjecting the resulting compound to one or more of the following operations:

i) removal of the protecting group $R^2$, ii) conversion of $X^aR^{7a}$ or $Z^aR^{7a}$ to $XR^7$ or $ZR^7$ respectively, and iii) conversion of the resultant compound of formula (I) into a pharmaceutically acceptable salt thereof.

10. A pharmaceutical composition comprising a compound according to claim 1 or a pharmaceutically acceptable salt thereof in admixture with one or more pharmaceutically acceptable carriers or excipients.

11. A method for the treatment of the human or non-human animal body to combat a bacterial infection comprising administration to said human or non-human animal body of an effective amount of a compound according to claim 1 or a pharmaceutically acceptable salt thereof.

12. A compound of gene*al formula (IA)

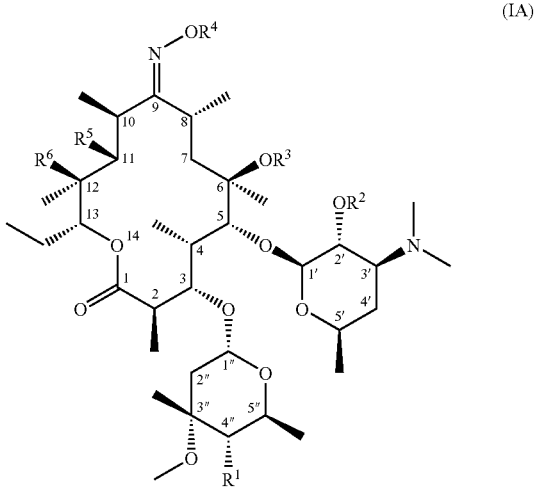

(IA)

wherein $R^1$ is OC(O)(CH$_2$)$_m$XR$^7$;

$R^2$ is hydrogen or a hydroxyl protecting group;

$R^3$ is hydrogen, $C_{1-4}$alkyl or $C_{3-6}$alkenyl optionally substituted by 9 to 10 membered fused bicyclic heteroaryl;

$R^4$ is hydrogen, $C_{1-4}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, $OR^8$, $S(O)_nR^8$, $NR^8R^9$, $CONR^8R^9$, halogen and cyano;

$R^5$ is hydroxy, $C_{3-6}$alkenyloxy optionally substituted by 9 to 10 membered fused bicyclic heteroaryl or O(CH$_2$)$_p$O(CH$_2$)$_q$R$^{10}$, $R^6$ is hydroxy, or $R^5$ and $R^6$ taken together with the intervening atoms form a cyclic group having the following structure:

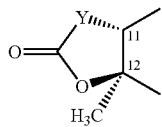

wherein Y is a bivalent radical selected from —CH$_2$—, —CH(CN)—, —O—, —N(R$^{11}$)— and —CH(SR$^8$)—;

R$^7$ is a heterocyclic group having the following structure:

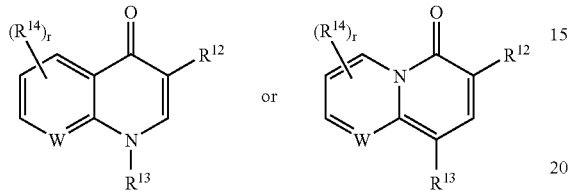

R$^8$ and R$^9$ are each independently selected from hydrogen and C$_{1-4}$alkyl;

R$^{10}$ is hydrogen or NR$^8$R$^9$;

R$^{11}$ is hydrogen or C$_{1-4}$alkyl substituted by a group selected from optionally substituted phenyl, optionally substituted 5 or 6 membered heteroaryl and optionally substituted 9 to 10 membered fused bicyclic heteroaryl;

R$^{12}$ is hydrogen, C(O)OR$^{15}$, C(O)NHR$^{15}$ or C(O)CH$_2$NO$_2$;

R$^{13}$ is hydrogen C$_{1-4}$alkyl, C$_{3-7}$cycloalkyl, or optionally substituted phenyl or benzyl;

R$^{14}$ is halogen, C$_{1-4}$alkyl, C$_{1-4}$thioalkyl, C$_{1-4}$alkoxy, NH$_2$, NH(C$_{1-4}$alkyl) or N(C$_{1-4}$alkyl)$_2$;

R$^{15}$ is hydrogen or C$_{1-4}$alkyl;

R$^{16}$ is hydrogen, C$_{1-4}$alkyl, C$_{3-7}$cycloalkyl, optionally substituted phenyl or benzyl, acetyl or benzoyl;

X is —U(CH$_2$)$_s$Z- or X is a group selected from:

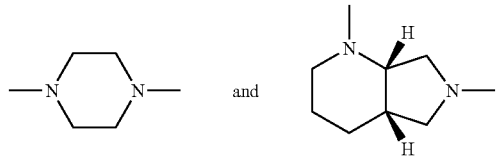

U and Z independently are a divalent radical selected from —N(R$^{16}$)—, —O—, —S(O)$_t$—, —N(R$^{16}$)C(O)—, —C(O)N(R$^{16}$)— and —N[C(O)R$^{16}$]—;

W is a carbon or a nitrogen atom;

m is 0 or an integer from 1 to 5;

n, r and t are each independently selected from 0, 1 and 2;

p and q are each independently selected from 1 and 2; and s is an integer from 2 to 8;

or a pharmaceutically acceptable salt thereof.

\* \* \* \* \*